United States Patent [19]
Arndt et al.

[11] Patent Number: 5,151,532
[45] Date of Patent: Sep. 29, 1992

[54] PROCESS FOR THE PRODUCTION OF HIGH-PURITY TETRACHLORO-1,4-BENZOQUINONE

[75] Inventors: Otto Arndt, Hofheim am Taunus; Theodor Papenfuhs, Frankfurt am Main, both of Fed. Rep. of Germany

[73] Assignee: Hoechst Aktiengesellschaft, Frankfurt am Main, Fed. Rep. of Germany

[21] Appl. No.: 724,499

[22] Filed: Jun. 27, 1991

Related U.S. Application Data

[63] Continuation of Ser. No. 151,893, Feb. 3, 1988, abandoned.

[30] Foreign Application Priority Data

Feb. 6, 1987 [DE] Fed. Rep. of Germany ....... 3703567

[51] Int. Cl.$^5$ .................... C07C 50/24; C07C 46/06
[52] U.S. Cl. .................... 552/308; 568/765
[58] Field of Search .................... 552/308

[56] References Cited

U.S. PATENT DOCUMENTS 2,722,537 1/1955 Fox .................... 260/396 R

FOREIGN PATENT DOCUMENTS 2933119 2/1981 Fed. Rep. of Germany ... 260/396 R

*Primary Examiner*—Vivian Garner
*Attorney, Agent, or Firm*—Connolly and Hutz

[57] ABSTRACT

A process for the preparation of high-purity tetrachloro-1,4-benzoquinone by the action of hydrogen peroxide and hydrochloric acid on hydroquinone, which comprises causing 3.8 top 4.2 times the molar quantity of 30 to 37% hydrochloric acid and 1.9 to 2.1 times the molar quantity of 50 to 35% hydrogen peroxide, to act at 5 to 50° C. on 1 mole of hydroquinone in at least 12 times the molar quantity of 30 to 37% hydrochloric acid, then heating the resulting suspension, which essentially contains 2,5-dichlorohydroquinone, to 45 to 55° C. and again causing to act on it, at 50 to 95° C., 3.8 to 4.2 times the molar quantity of 30 to 37% hydrochloric acid and 1.9 to 2.1 times the molar quantity of 50 to 35% hydrogen peroxide, in each case based on the hydroquinone used, and finally adding to the suspension, which is now essentially composed of trichloro-1,4-benzoquinone, 1.9 to 2.1 times the molar quantity of hydrochloric acid of the said concentration range, and 0.95 to 1.05 times the molar quantity of hydrogen peroxide of the said concentration range, in each case based on the hydroquinone used, at 95 to 115° C., sufficiently slowly for no chlorine to escape.

8 Claims, No Drawings

PROCESS FOR THE PRODUCTION OF HIGH-PURITY TETRACHLORO-1,4-BENZOQUINONE

RELATED APPLICATION

This application is a continuation of U.S. application Ser. No. 151,893 filed Feb. 3, 1988, abandoned by Otto Arndt, and Theodor Papenfuhs for "Process for the Production of High-Purity Tetrachloro-1,4-Benzoquinone DESCRIPTION The present invention relates to a process for the production of high-purity tetrachloro-1,4-benzoquinone (designated "chloranil" below) from hydroquinone.

The production of chloranil from hydroquinone (1,4-dihydroxybenzene) or 1,4-benzoquinone or chlorinated 1,4-benzoquinone by the following processes, described in the literature, is known per se:

1. Chlorination of hydroquinone with concentrated hydrochloric acid and concentrated hydrogen peroxide in the presence of magnesium chloride (German Offenlegungsschrift 2,645,114);
2. Action of chlorine on hydroquinone in boiling concentrated hydrochloric acid (Chemiker Zeitung 56 (1932), page 569);
3. Action of hydrochloric acid and nitric acid (aqua regia) on hydroquinone (J. Chem. Soc. Japan 63 (1942), page 1441);
4. Reactions of antimony(V) chloride with hydroquinone (Chemiker Zeitung 104 (1980) No. 1, pages 13 and 14);
5. Action of hydrogen chloride, air and metal salts on hydroquinone (East German Patent No. 29,292);
6. Reaction of trichloro-1,4-benzoquinone with chlorine in the presence of iodine and water (Liebigs Annalen der Chemie, supplementary volume 6 (1867), 213);
7. treatment of a mixture of trichloro-1,4-benzoquinone and tetrachloro-1,4-benzoquinone with hydrogen chloride in glacial acetic acid and subsequent action of concentrated nitric acid (Beilstein 7, 637);
8. Action of concentrated hydrochloric acid and 35% hydrogen peroxide on 1,4-benzoquinone (Ann. Chimica applic. 22 (1932), 602);
9. Introduction of chlorine into a solution of hydroquinone in aqueous hydrochloric acid with added chromium trioxide (Naugatuck Chem. Comp., USA, German Patent 594,520, Friedlander 20, 2047, U.S. Pat. No. 1,918,328).

These known processes have, however, the following disadvantages:

Re 1 A very large excess of hydrochloric acid (96 times the molar quantity) is required, and a very high salt load results due to the addition of 7.4 times the molar quantity of magnesium chloride. Furthermore, the prescribed temperature/time control during the addition of hydrogen peroxide cannot be maintained because of the high heat of reaction. A repeat of this process using only 30 times the molar quantity of hydrochloric acid, 3 times the molar quantity of magnesium chloride and more suitable temperature control gave a qualitatively poor chloranil (melting point 215°-220° C., yield 95% of theory) with trichloro-1,4-benzoquinone and tetrachlorohydroquinone as impurities.

Re 2: The introduction of gaseous elementary chlorine into boiling concentrated hydrochloric acid leads to an extensive escape of elementary chlorine gas in the hydrogen chloride vapors and makes it necessary to use a large excess of chlorine.

The possibility of working under pressure (in an autoclave), not indicated in the cited literature reference, requires greater engineering and safety efforts (fully enamelled fittings, valves and pipe connections).

The quantity of 37% hydrochloric acid indicated there (28 times the molar quantity) is very high, but is evidently insufficient for obtaining a reaction mixture which can be stirred at 25° C. Under these conditions, the mixture solidifies with the formation of tetrachlorohydroquinone.

Re 3: In this process, about 25 times the molar quantity of mineral acid, composed of 15 times the molar quantity of hydrochloric acid and about 10 times the molar quantity of nitric acid, is used. The yield is only about 45-65% of theory (melting point 280° C.). There is no indication regarding the disposal of the excess acid (in particular of the nitrogen oxides).

Re 4: The use of antimony is toxicologically objectionable and requires expensive recovery. Moreover, phosgene is said to be formed in this process.

Re 5: In the cited patent itself, attention is drawn to the high consumption of auxiliaries and to the low yield. Moreover, the steam distillation consumes a lot of energy.

Re 6: The use of iodine makes the regeneration of the hydrochloric acid for re-use more difficult.

Re 7: The stagewise synthesis from quinone (here: trichloro-1,4-benzoquinone) and hydrochloric acid with subsequent oxidation (here: nitric acid) of the chlorinated hydroquinone (here: tetrachlorohydroquinone) to give the quinone, with the necessary interstage purification operations, is an extremely time-consuming process and is unsuitable as an industrial process.

Re 8: In the process, an initial treatment with concentrated hydrochloric acid (22 Be=37%) (11 times the molar quantity) for 20 hours is followed by a treatment with 35% hydrogen peroxide below 60° C. for 12 hours. Even though a high yield of chloranil (melting point 289° to 290° C.) is obtained, the production becomes very expensive because of the low space-time yield).

Re 9: In the process, hydroquinone in hydrochloric acid is oxidized with chromium(VI) oxide (20 g/mol) to quinhydrone and the latter is then chlorinated with elementary chlorine to chloranil, initially at 25° C. and finally while hot. In the light of the present demands for protection of the environment, the use of chromium(VI) oxide is no longer economically acceptable.

The above review of the state of the art shows that the known processes generally require a large excess of hydrochloric acid, in some cases even auxiliaries which pollute the environment, and unusual oxidizing agents as well as long reaction times.

It has now been found, surprisingly, that the consumption of materials (especially of hydrochloric acid and chlorinating agent) and the time taken can be considerably reduced and, moreover, a high-purity product can be obtained, when the chlorination and oxidation are weighted in terms of time and temperature in such a way that oxidation to quinhydrone or quinone is avoided until 2 chlorine atoms have been introduced, so that the introduction of the third chlorine atom takes place simultaneously with the oxidation to trichlorobenzoquinone.

The invention thus relates to an improved process for the production of high-purity tetrachloro-1,4-benzoquinone by causing 3.8 to 4.2 times, preferably 4 times, the molar quantity of 30 to 37% hydrochloric acid, preferably 37% hydrochloric acid, and 1.9 to 2.1 times, preferably twice, the molar quantity of 50 to 35% hydrogen peroxide, preferably 35% hydrogen peroxide, to act at 5° to 50° C., preferably 10° to 20° C., on 1 mole of hydroquinone in at least 12 times, preferably 12 times, the molar quantity of 30 to 37% hydrochloric acid, preferably 37% hydrochloric acid, then heating the resulting suspension, which essentially contains 2,5-dichlorohydroquinone, to 45° to 55° C. and again causing to act on it, at 50° to 95° C., 3.8 to 4.2 times, preferably 4 times, the molar quantity of 30 to 37% hydrochloric acid, preferably 37% hydrochloric acid, and 1.9 to 2.1 times, preferably twice, the molar quantity of 50 to 35% hydrogen peroxide, preferably 35% hydrogen peroxide, in each case based on the hydroquinone used, and finally adding to the suspension, which is essentially composed of trichloro-1,4-benzoquinone, 1.9 to 2.1 times, preferably twice, the molar quantity of hydrochloric acid of the said concentration range, preferably 37% concentration, and 0.95 to 1.05 times the molar quantity, preferably the equimolar quantity, of hydrogen peroxide of the said concentration range, preferably 35% concentration, in each case based on the hydroquinone used, at 95° to 115° C., preferably 105° C., sufficiently slowly for no chlorine to escape.

The reason for the improved process control is the exploitation of the higher solubilities of the monochlorinated to trichlorinated hydroquinones in the concentrated hydrochloric acid as compared with the corresponding monochlorinated to trichlorinated 1,4-benzoquinones.

Departures from the process according to the invention manifest themselves in an increased consumption of chlorinating agent and a poor quality of the chloranil (higher content of tetrachlorohydroquinone, 2,3- and 2,5-dichloro-1,4-benzoquinone, trichloro-1,4-benzoquinone and unknown secondary components) (measured by HPLC=high-performance liquid chromatography and HPTLC=high-performance thin-layer chromatography).

The more rapid reaction with the chlorinating agent due to the higher solubilities of the monochlorinated to trichlorinated hydroquinones is further assisted by the use of surface-active auxiliaries which are stable to acid and chlorine, and these also effectively suppress possible foaming of the reaction mixture. A secondary alkanesulfonate is suitable and preferred as such an auxiliary. The surface-active auxiliaries are advantageously used in a quantity of about 5 to 15 millimole per mole of hydroquinone employed.

The concentration of the hydrochloric acid is also of great importance, particularly at the start of the chlorination. At starting hydrochloric acid concentrations below 30%, highly colored reaction mixture are obtained, which finally give poor quality chloranil. An adequately high starting hydrochloric acid concentration lowers the reduction potential of the hydroquinones to such an extent that, in line with the purpose of the invention, they remain protected from premature oxidation to 1,4-benzoquinone until the third chlorine atoms has been introduced.

The hydrochloric acid concentration decreases during the conversion. This results in the reaction ending with a 20% hydrochloric acid, which can be regenerated azeotropically, when a 37% hydrochloric acid is started with.

As compared with the state of the art, the process according to the invention is economically and ecologically advantageous. The mother liquors are regenerated by distillation to give 20% hydrochloric acid. The regenerated acids are colorless, and contain at most traces of organic carbon and can be re-used at other points in the production. Apart from the wash filtrate and a distillation residue composed essentially of secondary alkalenesulfate, no further production residues, which have to be disposed of, are obtained.

The chloranil produced according to the invention is of high purity, as demonstrated by the melting point (281°-282° C.) and by the fact that it does not contain any tetrachlorohydroquinone.

C content: 29.3 - 29.7% (theoretically 29.31%),
Cl content: 57.3 - 57.6% ("57.67%)
Purity (by titanometry) = 100.0%.

A preferred embodiment of the process according to the invention will now be given, parts being parts by weight:

1 part of hydroquinone is initially reacted at 10° C. with only about 2 parts of 35% hydrogen peroxide (corresponds to twice the molar quantity, based on the hydroquinone used) in 10.6 parts of 37% hydrochloric acid (corresponds to 12 times the molar quantity, based on the hydroquinone used) in the presence of about 0.025 parts of secondary alkanesulfonate. The reaction is highly exothermic. A white suspension composed of 64 mol % of 2,5-dichlorohydroquinone,
23 mol % of 2,3-dichlorohydroquinone and
13 mol % of 2-chlorohydroquinone is formed. The suspension is heated to 50° C. While heating further to 95° C., a further approximately 2 parts of 35% hydrogen peroxide are metered in, the reaction initially still being exothermic. The suspension changes color from white to pale brown. The foaming which occurs at this point is effectively suppressed by the presence of the secondary alkanesulfonate. In this phase 2,3,5-trichlorohydroquinone and 2,3,5-trichloro-1,4-benzoquinone are produced together virtually simultaneously. The 4th chlorine atom is then introduced at 105° C. with about 1 part of 35% hydrogen peroxide. A total of about 5.3 mole of hydrogen peroxide, based on the hydroquinone used, are used.

After filtration and washing, pure chloranil is obtained in a yield of 98% of theory, based on hydroquinone used. The off-gas contains only traces of elementary chlorine, corresponding to the excess hydrogen peroxide metered in at the end (about 3 to 4 mol-%, based on hydroquinone used). It contains no hydrogen chloride. The approximately 17 to 20% mother liquor is processed to give distilled approximately 18 to 20% hydrochloric acid. The only production residues obtained are the secondary alkanesulfonate used (distillation residue from the hydrochloric acid regeneration) and the wash filtrate. The latter is biodegradable (residual COD (chemical oxygen demand) = 6.1 kg of oxygen ($O_2$) per tonne of chloranil).

Chloranil is a valuable intermediate for the production of dyes and pesticides. It is also used as a photochemical and vulcanizing agent, and serves as lubricant additive.

The example which follows and the comparison example indicated serve to illustrate the invention in more detail.

EXAMPLE 100 parts of 35% hydrogen peroxide (1.0 mole) are introduced in 120 minutes at 10° C. with external cooling (5° C.) into a mixture of 592 parts of 37% hydrochloric acid (6.0 mole), 55.6 parts of hydroquinone (0.5 mole) and 1.4 parts of secondary n-alkanesulfonate (for example $C_{13-17}$). The mixture is then stirred for a further 30 minutes at 10° C. It is then heated at a constant rate to 50° C. in 30 minutes. Thereafter a further 100 parts of 35% hydrogen peroxide are metered into the white suspension (dichlorohydroquinone) in 60 minutes, simultaneously allowing the temperature to rise, initially due to the evolution of heat, and finally applying external heating to a temperature of 95° C. The suspension, which is now pale brown, mobile and non-foaming, is then heated to 105° C. in 60 minutes. At the same time, 25 parts of 35% hydrogen peroxide (0.25 mole) are added (heating bath at 110° C.). The suspension is now pale yellow. The mixture is then stirred at 105° C. for 240 minutes, during which time a maximum of 35 parts of 35% hydrogen peroxide (0.36 mole) must be further added, depending on the progress of conversion (the progress of the chlorination and oxidation is followed by HPTLC). The chlorination takes 9 hours.

After the end of the reaction, the residual chlorine gas present in the reactor atmosphere is flushed into a receiver containing 250 parts of water and 150 parts of 33% sodium hydroxide solution (0.02 mole of $Cl_2$). The off-gas does not contain any hydrochloric acid.

Filtration at 90° to 95° C. and washing with 600 parts of water results in 121 parts of pure chloranil (0.49 mole).

C content: 29.3 - 29.7% (theoretically 29.31%),
Cl content: 57.3 - 57.6% ( 57.67%),
Purity (by titanometry)=100%,
Melting point: 281°-282° C.

The mother liquor (781 parts of 17% hydrochloric acid) is distilled down to a residue under normal pressure. This gives 724 parts of 18% hydrochloric acid (colorless, organic carbon=75 mg/l) and 6.0 parts of distillation residue which can be removed from the distillation flask by means of water. The wash filtrate is biodegradable.

COMPARISON EXAMPLE

The process is carried out as described in the example, but with the difference that 170 parts, in place of only 100 parts, of 35% hydrogen peroxide (1.75 mole) are added at 10° C. in 240 minutes. A dark violet suspension is obtained. After the warming to 20° C., the mixture is heated to 50° C. in 60 minutes, simultaneously adding 24 parts of 35% hydrogen peroxide (0.25 mole). The suspension changes color to grayish brown, olive-colored and then yellow.

Addition of 36 parts of 35% hydrogen peroxide at 50 to 95° C. (45 minutes), 36 parts at 95° C. (60 minutes), 36 parts at 95 to 105° C. (360 minutes) (a total of 302 parts) and the usual working up result in 120 parts of chloranil of melting point 281° to 282° C. and with a chlorine content which is too low at 56.4% (theoretically 57.7%).

We claim:

1. A process for the preparation of high-purity tetrachloro-1,4-benzoquinone by the action of hydrogen peroxide and hydrochloric acid on hydroquinone, which comprises causing 3.8 to 4.2 times the molar quantity of 30% to 37% hydrochloric acid and 1.9 to 2.1 times the molar quantity of 50% to 35% hydrogen peroxide, to act at 5° C. to 50° C. on 1 mole of hydroquinone in at least 12 times the molar quantity of 30% to 37% hydrochloric acid, then heating the resulting suspension, which essentially contains 2,5-dichlorohydroquinone, to 45° C. to 55° C. and again causing to act on the resulting suspension, at 50° C. to 95° C., 3.8 to 4.2 times the molar quantity of 30% to 37% hydrochloric acid and 1.9 to 2.1 times the molar quantity of 50% to 35% hydrogen peroxide, in each case based on the hydroquinone used, and finally adding to the suspension, which is now essentially composed of trichloro-1,4-benzoquinone, 1.9 to 2.1 times the molar quantity of hydrochloric acid of the said concentration range, and 0.95 to 1.05 times that molar quantity of hydrogen peroxide of the said concentration range, in each case based on the hydroquinone used, at 95° C. to 115° C., sufficiently slowly for no chlorine to escape, the process being carried out in the presence or absence or a secondary alkanesulfonate.

2. The process of claim 1, wherein said secondary alkanesulfonate has 13 to 17 carbons.

3. The process as claimed in claim 1, wherein said hydrochloric acid is used in the amount of 4 times the molar quantity of the hydroquinone.

4. The process as claimed in claim 1, wherein said hydrochloric acid is at a concentration of 37%.

5. The process as claimed in claim 1, wherein said hydrogen peroxide is used in the amount of 2 times the molar quantity of the hydroquinone.

6. The process as claimed in claim 1, wherein said hydrogen peroxide is at a concentration of 35%.

7. The process of claim 1, wherein said initial step of causing 3.8 to 4.2 times the molar quantity of 30% to 37% hydrochloric acid and 1.9 to 2.1 times the molar quantity of 50% to 35% hydrogen peroxide to act on 1 mole of hydroquinone in at least 12 times the molar quantity of 30% to 37% hydrochloric acid occurs at a temperature ranging from 10° C. to 20° C.

8. The process as claimed in claim 1, wherein said hydrochloric acid is present at 12 times the molar quantity of the hydroquinone.

* * * * *